US00PP35969P2

(12) United States Plant Patent
Muñoz et al.

(10) Patent No.: US PP35,969 P2
(45) Date of Patent: Jul. 9, 2024

(54) BLUEBERRY PLANT NAMED 'FL19-006'

(50) Latin Name: ***Vaccinium corymbosum* L.**
Varietal Denomination: FL19-006

(71) Applicant: Florida Foundation Seed Producers, Inc., Marianna, FL (US)

(72) Inventors: Patricio Muñoz, Gainesville, FL (US); James W. Olmstead, Aptos, CA (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 0 days.

(21) Appl. No.: 18/473,008

(22) Filed: Sep. 22, 2023

(51) Int. Cl.
*A01H 5/08* (2018.01)
*A01H 6/36* (2018.01)

(52) U.S. Cl.
USPC ..... Plt./157

(58) Field of Classification Search
USPC ..... Plt./157
See application file for complete search history.

(56) References Cited

U.S. PATENT DOCUMENTS

PP12,165 P2 10/2001 Lyrene

OTHER PUBLICATIONS

U.S. Appl. No. 18/473,003, filed Sep. 22, 2023, Muñoz et al.

*Primary Examiner* — Susan McCormick Ewoldt
(74) *Attorney, Agent, or Firm* — Dentons US LLP

(57) ABSTRACT

'FL19-006' is a new and distinct southern highbush blueberry (*Vaccinium corymbosum* L.) variety distinguished at least by a low to very low chilling requirement, vigorous and healthy, compact bushy growth habit with good evergreen production, high early yield, good field disease resistance, and large fruit that have a balanced sweet to acid flavor with high wax cover that exhibits small picking scars.

6 Drawing Sheets

Latin name of the genus and species of the plant claimed: *Vaccinium corymbosum* L.

Variety denomination: 'FL19-006'.

BACKGROUND OF THE INVENTION

The invention relates to a new and distinct hybrid variety of southern highbush blueberry (*Vaccinium corymbosum* L.) plant 'FL19-006'. 'FL19-006' originated as a seedling that was generated from a cross performed in Gainesville, FL during February 2016 between 'FL13-212' (unpatented), as the female (seed) parent, and 'FL10-15' (unpatented), as the male (pollen) parent. The seedling was planted in a high-density field nursery in June 2017, and the first fruit were evaluated and selected in April of 2018. After the second year of fruiting in the field 'FL19-006' was propagated by softwood stem cuttings during the spring of 2019 to establish an experimental 15-plant test plot for a variety test that was conducted during January of 2020 in Waldo, FL, and a 5-plant plot in Arcadia, FL. It was during this variety test that the experimental code 'FL19-006' was assigned. Based on the growth, yield and fruit quality of this plot, 'FL19-006' was re-propagated by softwood stem cuttings and additional experimental test plots ranging from 5 to 45 plants were established for experimental research trials throughout Florida in 2021. These plots have been observed during flowering and ripening each year since establishment, and no mutations or off-type plants have been observed.

SUMMARY OF THE INVENTION

'FL19-006' differs from its parents and all other known southern highbush blueberry plants. The following are the most distinguishing characteristics of 'FL19-006' when grown under normal horticultural practices in Florida: (1) no to low chilling requirement, particularly for the flower buds; (2) a vigorous, compact round bushy growth habit; (3) high yield during the months of March and April; (4) large, firm, sweet berries that exhibit small to medium picking scars and strong waxy cover; and (5) extended tested postharvest fruit quality holding for up to 49 days.

'FL19-006' plants can be readily and unambiguously distinguished from those of its parents at least based upon earliness, higher yield, and quality of fruit. The early fruit yield exhibited by plants of 'FL19-006' is significantly earlier and higher yield than that of either 'FL13-212' and 'FL10-15'.

Blueberry variety 'Emerald' (U.S. Plant Pat. No. 12,165) is planted throughout the southeastern United States. Plants of 'FL19-006' and 'Emerald' can be readily and unambiguously distinguished at least based upon plant vigor, precociousness, the time at which their fruit is produced, as well as their fruit shape and cluster tightness. Plants of 'FL19-006' display significant more vigor and precociousness than 'Emerald'. Plants of 'FL19-006' produce their fruit significantly earlier than those of 'Emerald' when no growth regulator is used, and the fruit of 'FL19-006' are rounder and with looser clusters compared to 'Emerald'.

BRIEF DESCRIPTION OF THE DRAWINGS

'FL19-006' is illustrated in the accompanying photographs, which show the plant's flowers, fruit, leaves, and form. Colors shown are as true as can be reasonably reproduced by photographic procedures and may differ from those cited in the detailed description, which accurately describe the colors of 'FL19-006'.

DETAILED BOTANICAL DESCRIPTION

Figure 1:
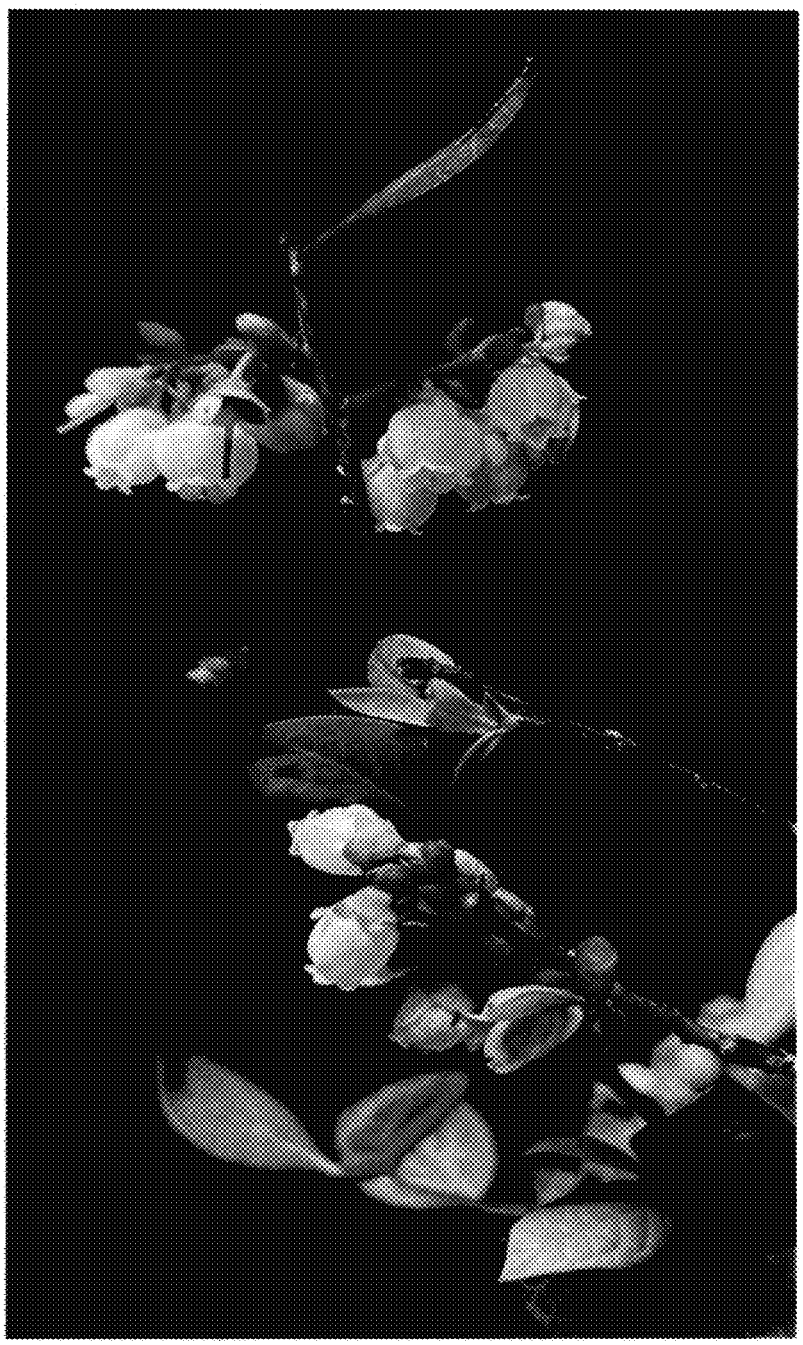
FIG. 1—Shows clusters of opening 'FL19-006' flowers.
Figure 2:
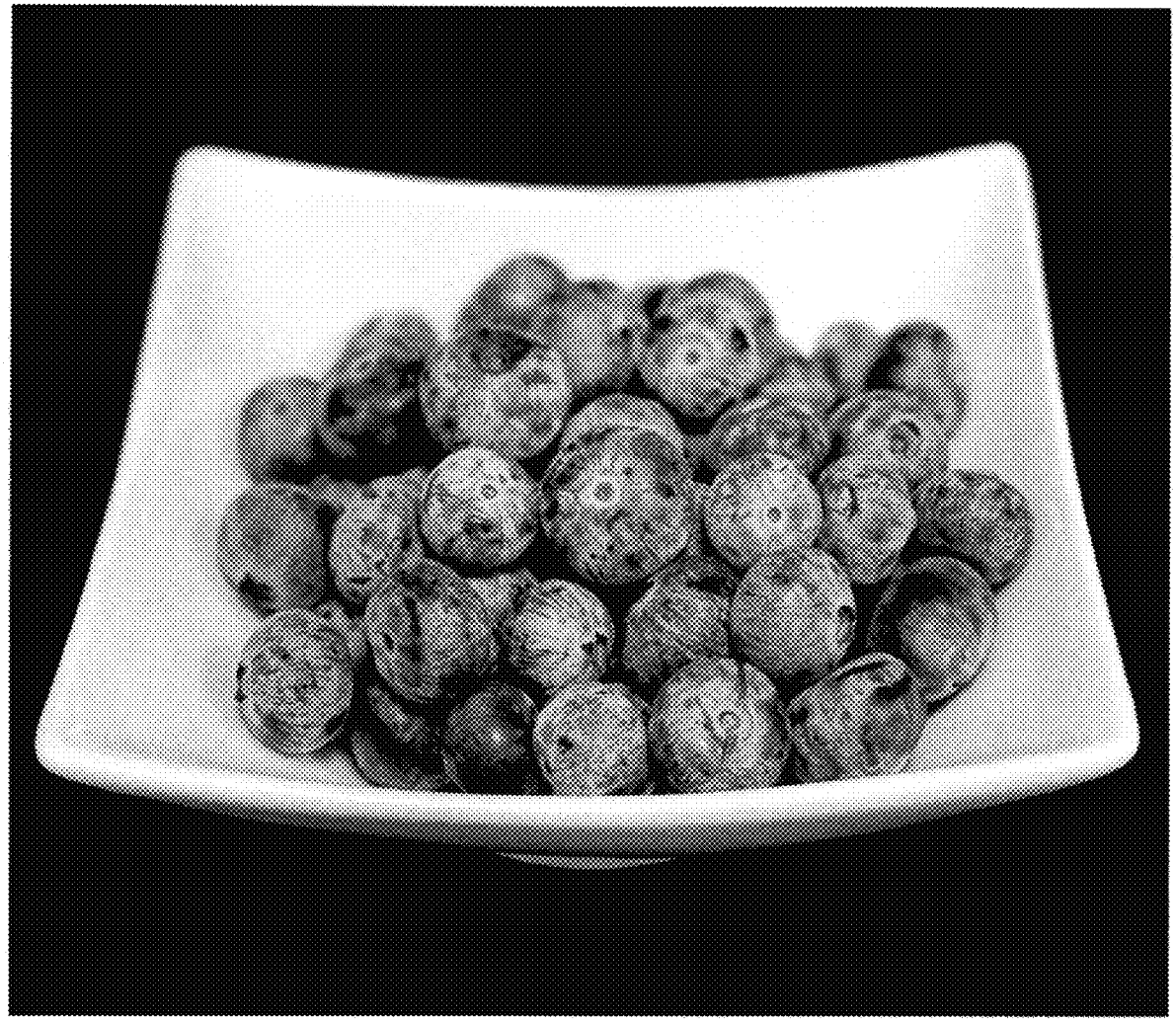
FIG. 2—Shows a close-up of harvested 'FL19-006' berries.
Figure 3:
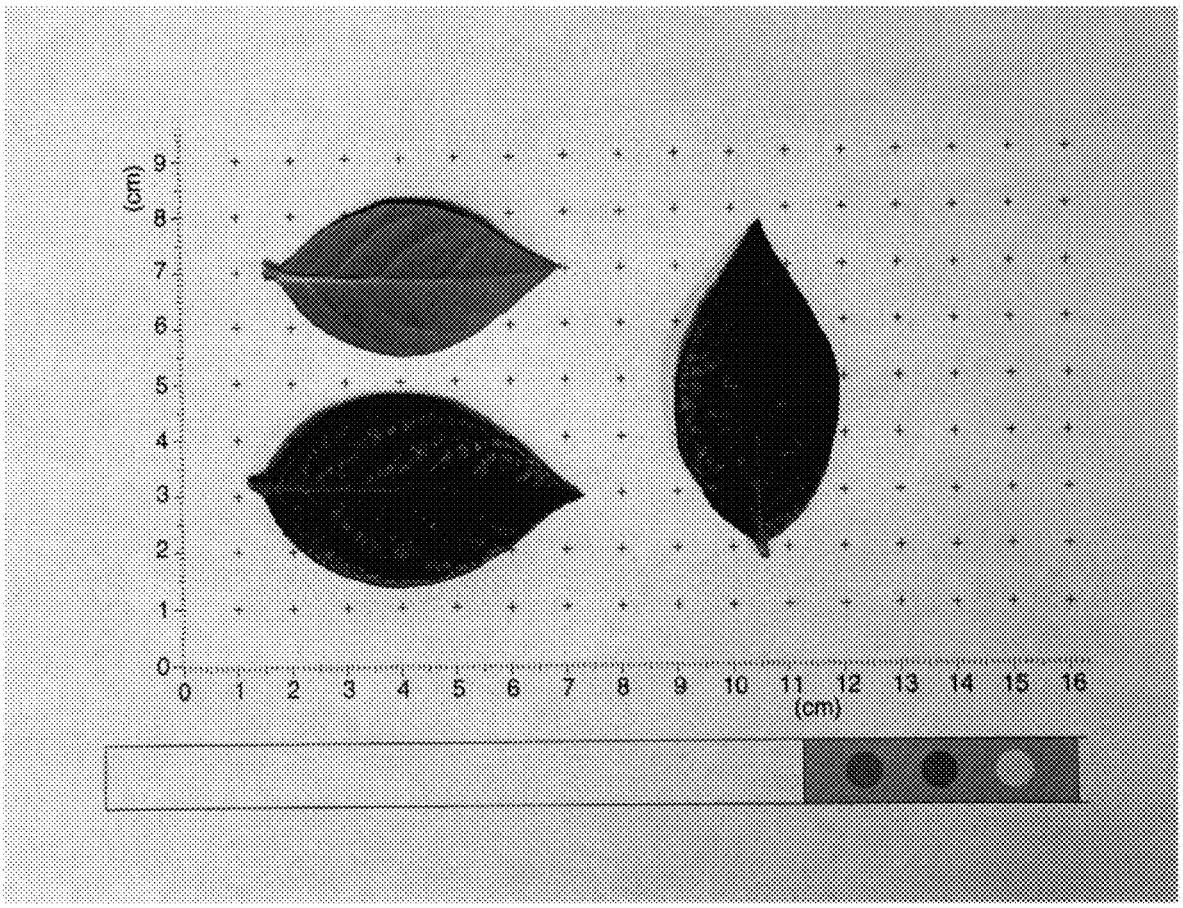
FIG. 3—Shows a close-up of mature 'FL19-006' leaves with a scale bar.
Figure 4:
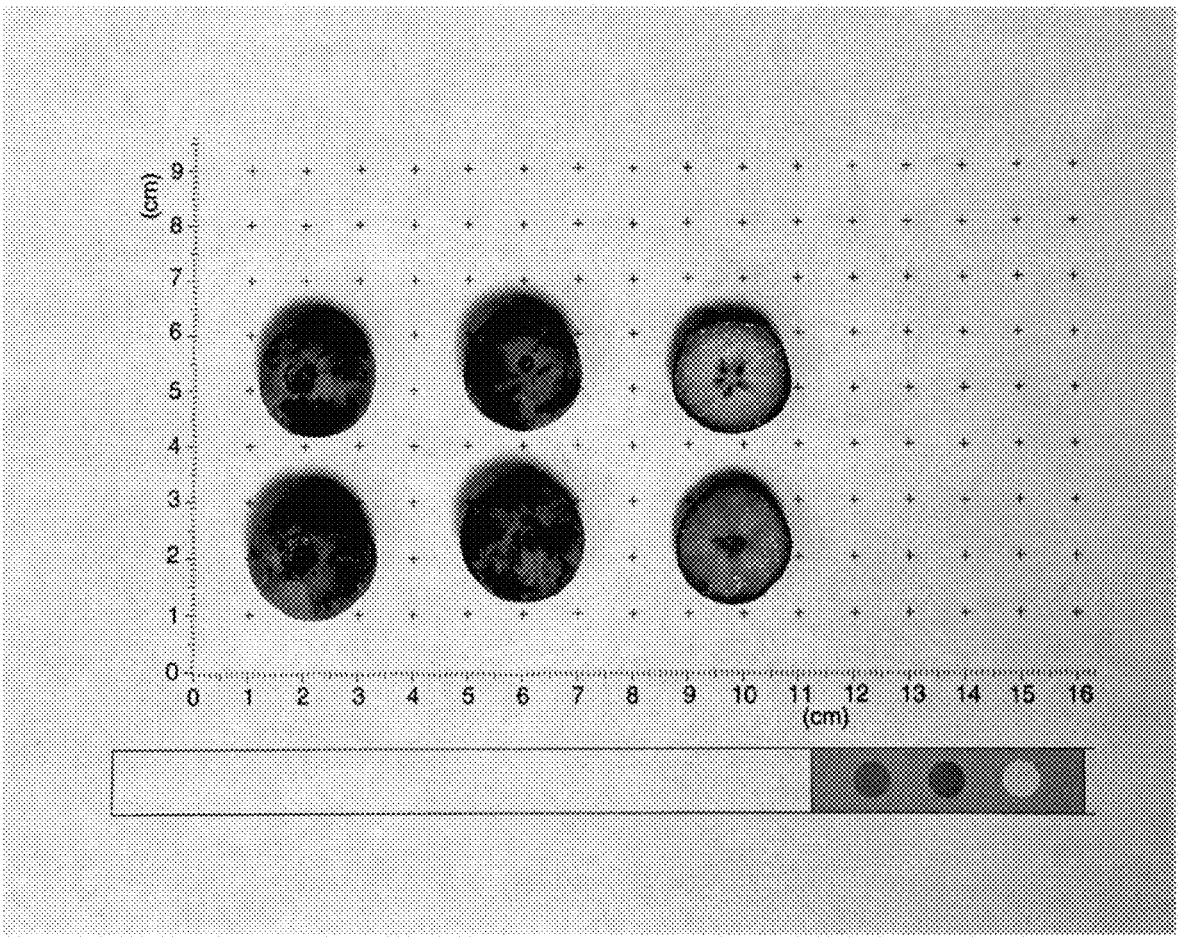
FIG. 4—Shows a close-up of mature 'FL19-006' fruit with a scale bar.
Figure 5:
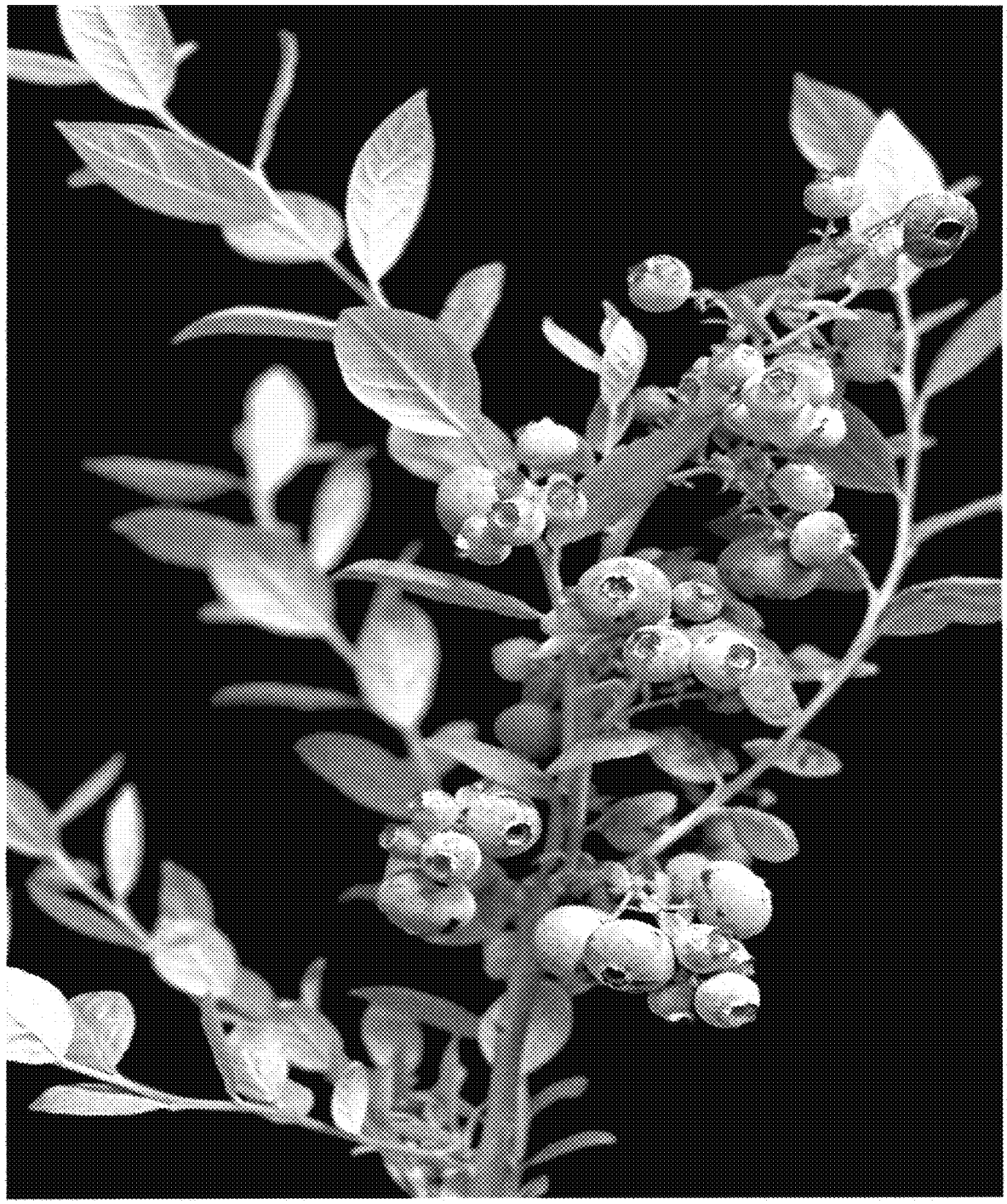
FIG. 5—Shows a close-up of ripening 'FL19-006' fruit on the plant.
Figure 6:
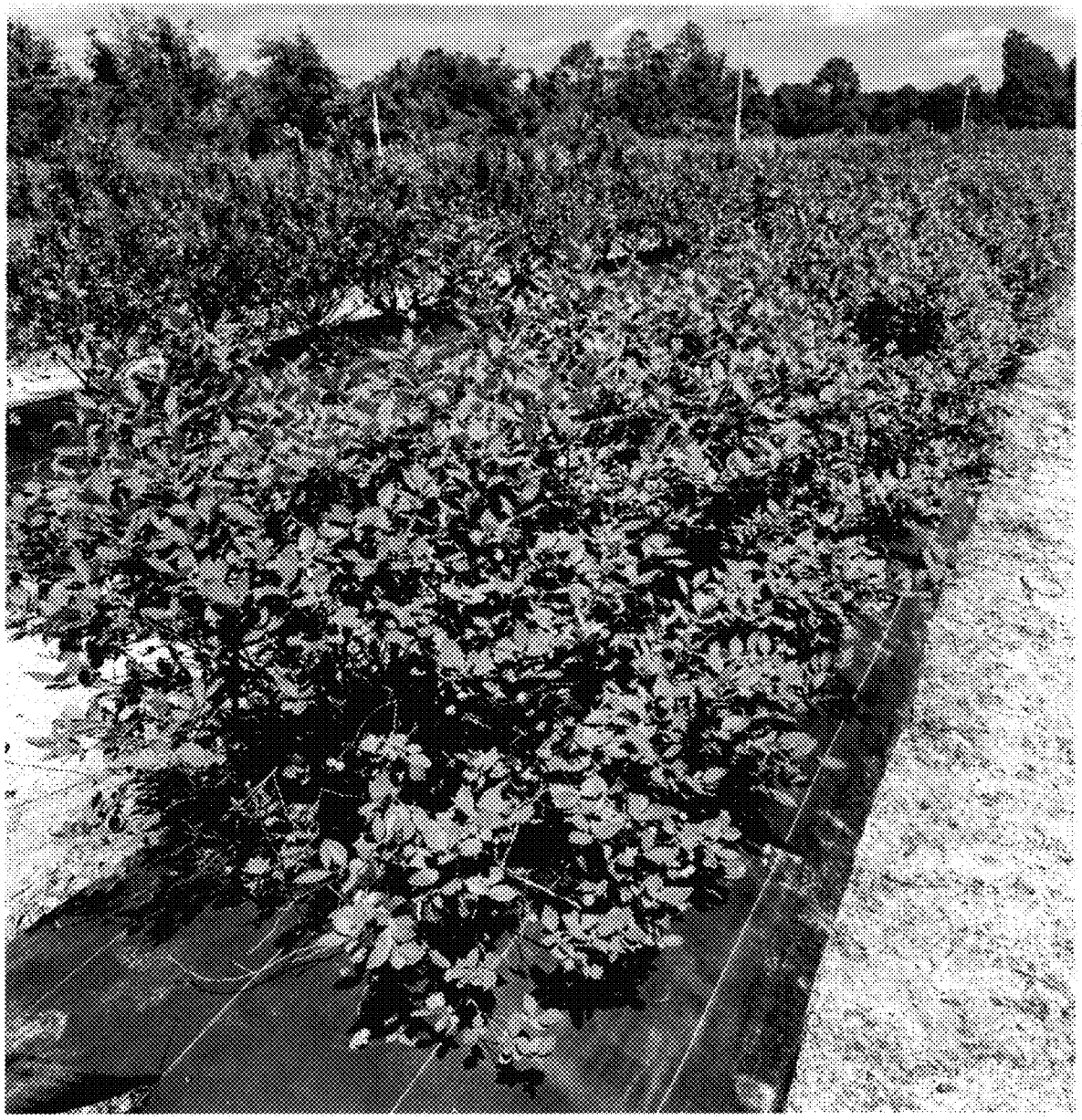
FIG. 6—Shows several Three-year-old 'FL19-006' plants in March 2023 with the vigorous, compact-bushy architecture and its potential productivity.

The following detailed description sets forth distinctive characteristics of 'FL19-006'. The data that define these characteristics were collected from asexual reproduction plants established in Florida. The plant history was taken on a plot of plants growing in an experimental trial in Waldo, Florida. The plants were 3 years of age when the data was collected. Certain characteristics may vary with plant age. 'FL19-006' has not been observed under all possible environmental conditions, and the measurements given may vary when grown in different environments. Color descriptions are based on The Royal Horticultural Society (R.H.S.) Color Chart by The Royal Horticultural Society, London, 6th Edition, (2015). If any R.H.S. color designations below differ from the accompanying photographs, The R.H.S. color designations are accurate.

Classification:

*Family*.—Ericaceae.

*Botanical*.—*Vaccinium corymbosum* L.

*Common name*.—Southern Highbush Blueberry.

*Cultivar name*.—'FL19-006'.

Plant:

*Plant vigor*.—High.

*Growth habit*.—Compact, round bush architecture.

*Plant height*.—1.3 m on average for 3-year-old plant.

*Plant spread*.—1.3 m on average for 3-year-old plant.

*Flower bud density* (*number*) *along flowering twigs in January*.—High.

*Twigginess*.—Low.

*Tendency toward evergreen-ness*.—Medium-High, Evergreen Candidate.

*Productivity*.—In northeast Florida, 'FL19-006' produces 6.7 kg/bush per season from plants 3 years old when hand harvested.

*Chilling requirement*.—It has been observed producing high yields in years of chill (below 7° C.) around 100-150 hours in north Florida and 0-50 in south Florida.

*Cold hardiness*.—'FL19-006' has been grown in temperate climates with extremely cold winter temperatures. Plants have survived winter freezes of −5° C. with minimal damage.

*Ease of propagation*.—'FL19-006' has only been propagated from softwood stem cuttings, where the rooting percentage is greater than 80% and comparable to other varieties.

Trunk and branches:

*Suckering tendency*.—Low.

*Surface texture* (*of strong, 12-month-old shoots observed*).—Moderate smooth. (Little to no presence of ridges and bark-like structure).

*Surface texture* (*of 3-year-old and older wood*).—Moderate rough texture with presence of bark with some flaking bark edges (erect quality to the bark edges).

*Color of new twigs observed in the field*.—Fan 4 Greyed-Orange Group 165 Brownish Orange B.

*Color of 3-year-old, rough-textured canes*.—Fan 4 Brown Group N200 Light Brownish Grey C.

*Internode length* (*strong, upright shoots*).—Mean of 18.04 mm.

Leaves:

*Leaf arrangement*.—Alternate, Fibonacci Spiral.

*Length* (*including petiole, from tip of petiole to end of blade*).—Mean of 5.54 cm.

*Width* (*at widest point*).—Mean of 3.14 cm.

*Petiole length*.—Mean of 2.40 mm.

*Petiole diameter*.—Mean of 1.48 mm.

*Leaf shape*.—Elliptic, with the leaf apex having a small point. The leaf is slight falcate at the leaf apex. There is a presence of a small tip extension at the leaf apex. The leaf tip extension had a mean of 0.46 mm.

*Leaf base shape*.—Elliptic.

*Leaf venation pattern*.—Reticulate

*Margin*.—Entire.

*Color*.—Upper surface: Fan 3 Green Group 137 Moderate Olive Green A. Lower surface: Fan 4 Greyed-Green Group 191 Greyish Yellow Green B. Leaf Vein Color: Fan 3 Yellow -Green Group 145 Light Yellow Green C. Leaf petiole color: Fan 3 Yellow-Green Group 145 Light Yellow Green C. with some hints of Fan 2 Red Purple Group 61 Vivid Purplish Red C on the sides of the leaf petiole and on the leaf veining at the base of the leaf. (Some observed anthocyanin presence on leaf veining predominantly at the base of the leaf and on the sides of the petiole).

*Pubescence*.—Upper surface of leaves: Absent. Lower surface of leaves: Absent. Margins: Absent.

*Timing of vegetative bud burst* (*early, medium, late*).—Early.

*Relative time of leafing versus flowering*.—When not treated with hydrogen cyanamide in mid-winter, leafing occurs during flowering.

*Leaf glaucosity*.—High.

Flowers:

*Inflorescence* (*small, med, large*).—Medium.

*Arrangement*.—Flowers are arranged medium tight clusters of flowers spiraling along branches with leaves.

*Fragrance*.—Very slight floral fragrance.

*Shape*.—Urceolate-cylindrical with moderate radiations along the corolla. Some out-curving of the corolla tips at the corolla aperture.

*Flowering period*.—Mean date of 50% anthesis at Waldo, Fl is Dec. 29, 2022 (Week 52.5).

*Cluster*.—Medium tight cluster.

*Number of flowers per cluster*.—Mean of 4.

*Pedicel*.—Length at time of anthesis: Mean of 5.56 mm. Color at time of anthesis (Non sun exposed side): Fan 3 Yellow-Green Group 145 Light Yellow Green B with hints of Fan 2 Red-Purple Group 61 Deep Purplish Red A on the sun exposed side.

*Peduncle*.—Length at time of anthesis: Highly, variable, mean of 14.85 mm. Color at time of anthesis (Non sun exposed side): Fan 3 Yellow Green Group 144 Strong Yellow Green A. Sun-exposed Side: Fan 3 Yellow Green Group 144 Strong Yellow Green A with hints of Fan 2 Red Purple Group N57 Vivid Purplish Red B.

*Calyx*.—Surface texture: Very Smooth with moderate wax. Diameter: Mean of 6.03 mm. Color (outer surface, visible at the time of anthesis without removing the corolla tube): Fan 3 Yellow Green Group 145 Strong Yellow Green A. Receptacle Color: Fan 3 Green Group 143 Strong Yellow Green C.

*Corolla*.—Diameter: mean of 7.22 mm. Length (from pedicel attachment point to corolla tip excluding the pedicel): Mean of 10.72 mm. Aperture diameter: Mean of 2.95 mm. Texture: Smooth with radiations along the length of the corolla. Color: Fan 4 white group NN155 Yellowish White A. Anthocyanin coloration in tube: Some presence of anthocyanin on radial edges and on the tips of the corolla aperture.

Reproductive organs:

*Style*.—Length (top of ovary to stigma tip): Mean of 9.87 mm. Color: Fan 3 Yellow-Green Group 145 Light Yellow Green C.

*Location of tip pf stigma relative to lip of the corolla*.—Stigma tip is approximately Even to 0.30 mm below the corolla lip.

*Anthers*.—Color: Fan 4 Greyed-Orange Group N167 Moderate Orange C at the tip of the anther and Fan 4 Greyed-Orange N167 Brownish Orange B at the base of the anther. Pollen: High. Pollen germination: Typically, greater 90%. Color: Fan 1 Yellow Group 11 Pale Yellow D. Filament length: 4.36 mm. Filament width: 1.36 mm.

*Self-fruitfulness*.—Low to medium. Planting in the field configurations that promote cross fertilization with other southern highbush varieties is recommended for all southern highbush blueberry plants grown in Florida.

Fruit:

*Mean date of* 50% *harvest in Citra, Florida*.—Apr. 18, 2023.

*Diameter of calyx aperture on mature berry*.—Mean of 5.82 mm.

*Size and shape of calyx lobes on mature berry*.—Very small lobes with a high variable combination of being flat, incurving, and erect with a moderate shallow calyx basin.

*Pedicel length on ripe berry*.—Mean of 4.89 mm.

*Detachment force for ripe berries* (*easy, medium, hard*).—Easy.

*Fruit cluster density* (*sparse, medium, dense*).—Medium to dense.

*Number of berries per cluster*.—Mean of 4.

*Fruiting type*.—Fruiting observed on current season wood only.

Berry:

*Cluster* (*tight, medium, loose*).—Medium.

*Weight* (*on well-pruned plants*).—(25 berries) Mean of 87.66 g.

*Height*.—Mean of 15.58 mm.

*Width*.—Mean of 20.43 mm.

*Shape*.—Oblate.

*Surface color of mature berries ripe on the plant*.—Fan 2 Violet-Blue Group 97 Light Purplish-Blue B.

*Intensity of fruit bloom*.—High.

*Surface color of ripe berry after polishing*.—Fan 4 Black Group 203 Bluish Black C.

*Immature berry color, with bloom*.—Fan 3 Yellow Green Group 144 strong Yellow Green C.

*Immature berry color, without bloom*.—Fan 3 Yellow Green Group 145 Light Yellow Green C with hints of Fan 2 Red-Purple Group 63 Strong Purplish Red B.

*Flesh color*.—Fan 4 Green White Group 157 Pale-Yellow Green C.

*Surface wax*.—High and has high persistence.

*Pedicel scar*.—Small and dry. Mean of 1.87 mm.

*Firmness*.—Mean 298.23 g/mm.

*Flavor*.—Very balanced flavor of sweetness and tanginess with hints of some background volatiles.

*Intensity of fruit sweetness*.—Medium to high.

*Texture*.—Good texture (Juicy, non-mealy, fleshy) and no stone cells present. Very berry quality with a moderate bursting quality while eating.

*Fruit storage quality*.—Fruit is very firm and can be stored without shriveling, mold, or loss of firmness for 6 weeks at 4° C.

Seeds:

*Color of dried seeds*.—Fan 4 Greyed- Orange Group 165 Brownish Orange B.

*Weight of* 25 *well-developed dried seeds*.—Mean of 19.6 mg.

*Length of well-developed dried seeds*.—Mean of 2.076 mm.

*Width of well-developed dried seeds*.—Mean of 1.174 mm.

Use: Produces southern highbush blueberries suitable for hand harvest for the fresh fruit markets.

Resistance to diseases, insects, and mites: 'FL19-006' has grown vigorously and shows good bush survival in the field, with almost no young plants dying soon after planting. Reaction to the various fungal species that cause summer leaf spots (including rust) is lower than those of other southern highbush varieties. We have only observed lower levels of target spot (*Crynespora cassiicola*), but the plants seem tolerant to it. Fungicide applications may be needed after harvest to reduce foliar diseases and retain leaves into the fall for maximum flower bud set. Preliminary results of an experiment showed low levels of *Botrytis* spp. fruit susceptibility. Appears to be more tolerant than other southern highbush varieties to spider mites. Susceptibility to typical blueberry insect and mite pathogens such as spotted wing *Drosophila* (*Drosophila suzukii*), blueberry gall midge (*Dasineura oxycoccana*), blueberry chilly thrips (*Scirtothips dorsalis*), blueberry flower thrips (*Frankliniella* spp), and blueberry bud mite (*Acalitus vaccini*) appear similar to other southern highbush cultivars.

What is claimed is:

1. A new and distinct variety of southern highbush blueberry plant named 'FL19-006', as illustrated and described herein.

* * * * *